United States Patent [19]

Okada et al.

[11] Patent Number: 5,283,251
[45] Date of Patent: Feb. 1, 1994

[54] INDOLE DERIVATIVES

[75] Inventors: Satoshi Okada; Kozo Sawada; Natsuko Kayakiri; Yuki Saitoh, all of Tsukuba; Hirokazu Tanaka, Tsuchiura; Masashi Hashimoto, Tokyo, all of Japan

[73] Assignee: Fujisawa Pharmaceutical Co., Ltd., Osaka, Japan

[21] Appl. No.: 920,384

[22] Filed: Oct. 8, 1992

[30] Foreign Application Priority Data

Feb. 26, 1990 [GB] United Kingdom ........... 9004301

[51] Int. Cl.$^5$ ............... G61K 31/405; C07D 209/18; C07D 209/26
[52] U.S. Cl. .................... 514/415; 548/500; 548/502; 548/492; 548/494
[58] Field of Search ............ 548/500, 494, 502; 514/415

[56] References Cited

U.S. PATENT DOCUMENTS 3,259,622  7/1966  Shen ................. 260/247.5
3,544,563 12/1970  Yamamoto ............ 260/240

FOREIGN PATENT DOCUMENTS 1153570  5/1969  United Kingdom .
1159626  7/1969  United Kingdom .

Primary Examiner—David B. Springer
Attorney, Agent, or Firm—Oblon, Spivak, McClelland, Maier & Naustadt

[57] ABSTRACT

Indole derivatives of the following formula:

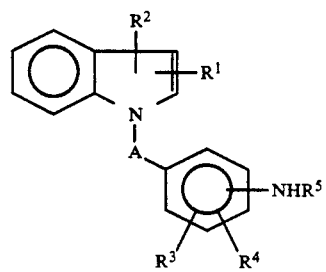

wherein
$R^1$ is carboxy(lower)alkyl or protected carboxy(lower)alkyl,
$R^2$ is hydrogen, lower alkyl or halogen,
$R^3$ and $R^4$ are each hydrogen or lower alkyl,
$R^5$ is ar(lower)alkyl which may have suitable substituent(s), and
A is carbonyl, sulfonyl or lower alkylene, or a pharmaceutically acceptable salt thereof, which are useful as a testosterone 5α-reductase inhibitor.

9 Claims, No Drawings

INDOLE DERIVATIVES

The present invention relates to novel indole derivatives and a pharmaceutically acceptable salt thereof. More particularly, it relates to novel indole derivatives and a pharmaceutically acceptable salt thereof which have pharmacological activities such as inhibitory activity on testosteron 5α-reductase and the like, to process for preparation thereof, to a pharmaceutical composition comprising the same and to a use of the same as a medicament.

Accordingly, one object of the present invention is to provide novel indole derivatives and a pharmaceutically acceptable salt thereof, which are useful as a testosteron 5α-reductase inhibitor.

Another object of the present invention is to provide process for preparation of said indole derivatives or a salt thereof.

A further object of the present invention is to provide a pharmaceutical composition comprising, as an active ingredient, said indole derivatives or a pharmaceutically acceptable salt thereof. Still further object of the present invention is to provide a use of said indole derivatives or a pharmaceutically acceptable salt thereof as a medicament such as testosteron 5α-reductase inhibitor useful for treating or preventing testosteron 5α-reductase mediated diseases such as alopecia, acnes, prostatism, and the like in human being or animals.

The indole derivatives of the present invention are novel and can be represented by the formula (I):

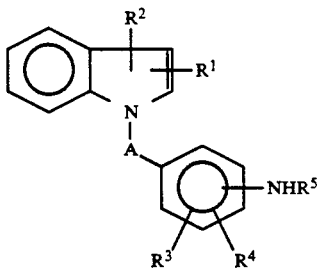

wherein $R^1$ is carboxy(lower)alkyl or protected carboxy(lower)alkyl, $R^2$ is hydrogen, lower alkyl or halogen, $R^3$ and $R^4$ are each hydrogen or lower alkyl, $R^5$ is ar(lower)alkyl which may have suitable substituent(s), and A is carbonyl, sulfonyl or lower alkylene.

According to the present invention, the object compound (I) can be prepared by the following process.

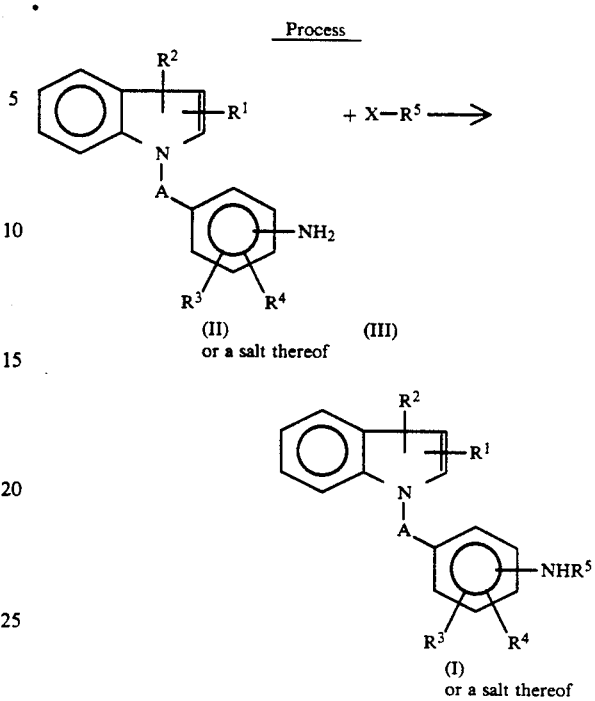

wherein
$R^1$, $R^2$, $R^3$, $R^4$, $R^5$ and A are each as defined above, and

X is acid residue.

Suitable salts of the compounds (I) are conventional non-toxic, pharmaceutically acceptable salt and may include a salt with a base or an acid addition salt such as a salt with an inorganic base, for example, an alkali metal salt (e.g. sodium salt, potassium salt, cesium salt, etc.), an alkaline earth metal salt (e.g. calcium salt, magnesium salt, etc.), an ammonium salt; a salt with an organic base, for example, an organic amine salt (e.g. triethylamine salt, pyridine salt, picoline salt, ethanolamine salt, triethanolamine salt, dicyclohexylamine salt, N,N'-dibenzylethylenediamine salt, etc.), etc.; an inorganic acid addition salt (e.g. hydrochloride, hydrobromide, sulfate, phosphate, etc.); an organic carboxylic or sulfonic acid addition salt (e.g. formate, acetate, trifluoroacetate, maleate, tartrate, methanesulfonate, benzenesulfonate, p-toluenesulfonate, etc.); a salt with a basic or acidic amino acid (e.g. arginine, aspartic acid, glutamic acid, etc.); and the like, and the preferable example thereof is an acid addition salt.

In the above and subsequent descriptions of the present specification, suitable examples and illustrations of the various definitions which the present invention include within the scope thereof are explained in detail as follows.

The term "lower" is intended to mean 1 to 6 carbon atoms, preferably 1 to 4 carbon atoms, unless otherwise indicated.

Suitable "lower alkyl" may include straight or branched one, having 1 to 6 carbon atom(s), such as methyl, ethyl, propyl, isopropyl, butyl, isobutyl, t-butyl, pentyl, hexyl, and the like, preferably one having 1 to 4 carbon atoms.

The term "carboxy(lower)alkyl" means lower alkyl as mentioned above, which is substituted by a carboxy group and suitable example thereof may include carboxymethyl, carboxyethyl, carboxypropyl, carboxybutyl, carboxypentyl, carboxyhexyl, and the like.

The term "protected carboxy(lower)alkyl" means the above-mentioned carboxy(lower)alkyl, in which the carboxy group is protected by a conventional protective group such as esterified carboxy group. Preferred example of the ester moiety thereof may include lower alkyl ester (e.g. methyl ester, ethyl ester, propyl ester, etc.), ar(lower)alkyl ester (e.g. trityl ester, benzhydryl ester, benzyl ester, etc.), and the like.

Suitable "ar(lower)alkyl which may have suitable substituent(s)" may include a conventional group such as ar(lower)alkyl (e.g. trityl, benzhydryl, benzyl, phenethyl, naphthylmethyl, etc.), substituted ar(lower)alkyl, for example, ar(lower)alkyl substituted by the group selected from lower alkyl as mentioned above and halogen as mentioned below [e.g. bis(methylphenyl)methyl, bis(propylphenyl)methyl, bis(butylphenyl)methyl, bis(isobutylphenyl)methyl, bis(chlorophenyl)methyl, etc.], and the like, preferably benzhydryl substituted by lower alkyl.

The term "halogen" means fluoro, chloro, bromo and iodo.

Suitable "lower alkylene" means straight or branched bivalent lower alkane such as methylene, ethylene, trimethylene, tetramethylene, pentamethylene, hexamethylene, propylene, and the like.

Suitable "acid residue" may include halogen (e.g. fluoro, chloro, bromo, iodo), acyloxy (e.g. acetoxy, tosyloxy, mesyloxy, etc.) and the like.

Particularly, the preferred embodiments of $R^1$, $R^2$, $R^3$, $R^4$, $R^5$ and A are as follows.

$R^1$ is carboxy(lower)alkyl, (e.g. carboxymethyl, 2-carboxyethyl, 3-carboxypropyl, 4-carboxybutyl, 5-carboxypentyl, etc.);

$R^2$ is hydrogen; lower alkyl, more preferably $C_1$-$C_4$ alkyl (e.g. methyl, etc.); or halogen (e.g. chloro, etc.), $R^3$ is hydrogen; or lower alkyl, more preferably $C_1$-$C_4$ alkyl (e.g. methyl, etc.), $R^4$ is hydrogen; or lower alkyl, more preferably $C_1$-$C_4$ alkyl (e.g. methyl, etc.), $R^5$ is ar(lower)alkyl, for example, mono or di or triphenyl(lower)alkyl, substituted by the group selected from lower alkyl and halogen, more preferably mono or di or triphenyl($C_1$-$C_4$)alkyl substituted by the group selected from $C_1$-$C_4$ alkyl and halogen [e.g. bis(propylphenyl)methyl, bis(isobutylphenyl)methyl, bis[chlorophenyl)methyl, etc.]; and A is carbonyl; sulfonyl; or lower alkylene, more preferably $C_1$-$C_4$ alkylene (e.g. methylene, etc.).

The radicals $R^1$ and $R^2$ on the indole skeleton of the compound (I) are attachable on optional positions thereof excepting 1-position.

The process for preparing the object compound (I) of the present invention is explained in detail in the following.

PROCESS

The object compound (I) or a salt thereof can be prepared by reacting the compound (II) or a salt thereof with the compound (III).

Suitable salts of the compound (II) can be referred to the salts as exemplified for the compound (I).

This reaction is usually carried out in a solvent such as alcohol [e.g. methanol, ethanol, etc.], dichloromethane, benzene, N,N-dimethylformamide, tetrahydrofuran, diethyl ether or any other solvent which does not adversely affect the reaction.

The reaction may be carried out in the presence of an inorganic or an organic base such as an alkali metal hydroxide [e.g. sodium hydroxide, potassium hydroxide, etc.], an alkali metal carbonate [e.g. sodium carbonate, potassium carbonate, etc.], an alkali metal bicarbonate [e.g. sodium bicarbonate, potassium bicarbonate, etc.], tri(lower)alkylamine [e.g. trimethylamine, triethylamine, ethyldiisopropylamine, etc.], pyridine or its derivative [e.g. picoline, lutidine, 4-dimethylaminopyridine, etc.], or the like. In case that the base to be used is liquid, it can also be used as a solvent.

The reaction temperature is not critical, and the reaction can be carried out under cooling, at room temperature or under warming or heating.

The starting compound (II) is new and can be prepared by the following methods, the details of which are shown in Preparations mentioned below, or a conventional manner.

Method A

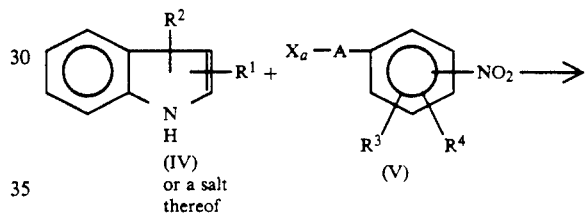

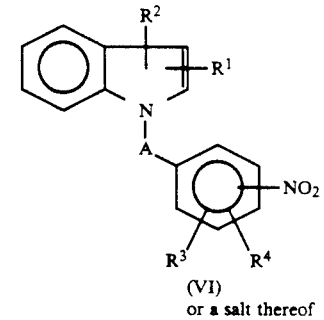

Method B

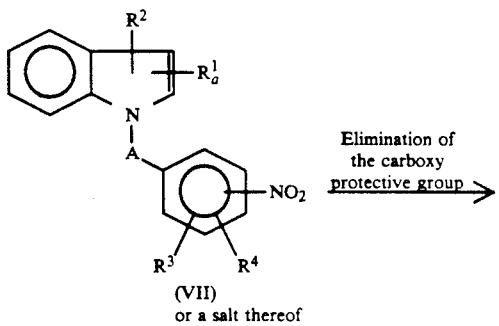

-continued

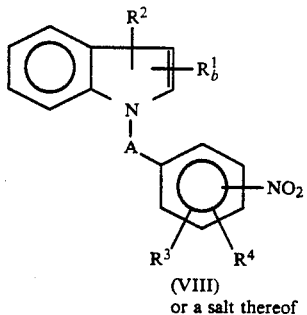

(VIII)
or a salt thereof

Method C

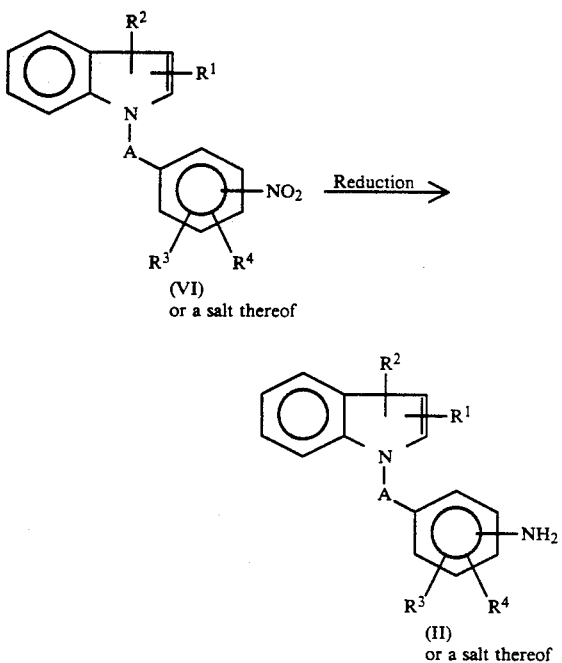

wherein $R^1$, $R^2$, $R^3$, $R^4$ and A are each as defined above,
$R_a^1$ is protected carboxy(lower)alkyl,
$R_b^1$ is carboxy(lower)alkyl, and
$X_a$ is acid residue.

Methods A, B and C can be carried out in a conventional manner.

The object compound (I) of the present invention can be isolated and purified in a conventional manner, for example, extraction, precipitation, fractional crystallization, recrystallization, chromatography, and the like.

The object compound (I) thus obtained can be converted to its salt by a conventional method.

The object compound (I) of the present invention is useful as a testosteron 5α-reductase inhibitor and effective to testosteron 5α-reductase mediated diseases such as prostatism, prostatic hypertrophy, prostatic cancer, alopecia, hirsutism (e.g. female hirsutism, etc.), androgenic alopecia (or male-pattern baldness), acne (e.g. acne vulgaris, pimple, etc.), other hyperandrogenism, and the like.

In order to illustrate the usefulness of the object compounds (I), pharmacological activity of representative compounds of the present invention is shown below.

[1] Test Compound

4-[1-[3-[Bis(4-isobutylphenyl)methylamino]benzoyl]indol-3-yl]butyric acid (hereinafter referred to as Compound ①)

[2] Inhibitory Activity on Testosterone 5α-Reductase in Rats

Test Methods i) Materials 1,2,6,7-$^3$H-Testosterone (85–105 Ci/mmol): 1,2,6,7-$^3$H-Testosterone (85–105 Ci/mmol) is a mixture of 1,2,6,7-$^3$H-testosterone and testosterone which includes 85–105 Ci of 1,2,6,7-$^3$H-testosterone per mmol of testosterone and is purchased from New England Nuclear, Boston, Mass., U.S.A..

Aquazol-2 (Aquazol-2 Universal LSC Cocktail): trademark, purchased from New England Nuclear, Boston, Mass., U.S.A.

ii) Preparation of Prostatic Testosterone 5α-Reductase

Mature Spraque-Dawley male rats (7–8 weeks old) were sacrificed by diethyl ether. The ventral prostates were dissected to be free of their capsules and their combined volume was measured by displacement in several milliliters of ice-cold medium A (0.32M sucrose, 0.1 mM dithiothreitol and 20 mM sodium phosphate, pH 6.5). Unless specified, all the following procedures were carried out at 0°–4° C. The prostates were drained, minced, and then homogenized in 3–4 tissue volumes of medium A with Pyrex-glass homogenizer. The homogenate was fractioned by differential centrifugations at 3,000 g for 15 minutes. The resulting pellets were resuspended in medium A. The suspension (20–30 mg protein/ml) was stored at −80° C.

iii) Testosterone 5α-Reductase Assay

The reaction solution contains 1 mM dithiothreitol, 40 mM sodium phosphate pH 6.5, 50 μM NADPH, 1,2,6,7-$^3$H-testosterone/testosterone ($2.2 \times 10^{-9}$M) and the suspension prepared above (0.8 mg of protein) in a total volume of 565 μl. Test Compound was added in 10 μl of 10% ethanol whereas control tubes received the same volume of 10% ethanol. The reaction was started with the addition of the enzyme suspension. After incubation at 37° C. for 30 minutes, the reaction was extracted with 1 ml of ethyl acetate. Fifty μl of ethyl acetate phase was chromatographed on a Merck silica plastic sheet Kieselgel 60 F$_{254}$, using ethyl acetate:cyclohexane (1:1) as the developing solvent system. The plastic sheet was air dried and cut the testosterone and the 5α-dihydrotestosterone areas. The radioactivity was counted in 5 ml of Aquazol-2 in Packard scintillation counter [PACKARD TRI - CARB 4530), and an inhibitory ratio was calculated.

[3] Test Results

| Compound | IC$_{50}$ (M) |
|---|---|
| ① | $7.6 \times 10^{-8}$ |

For therapeutic or preventive administration, the object compound (I) of the present invention are used in the form of conventional pharmaceutical preparation which contains said compound as an active ingredient, in admixture with pharmaceutically acceptable carriers such as an organic or inorganic solid or liquid excipient which is suitable for oral, parenteral and external administration. The pharmaceutical preparation may be in solid form such as tablet, granule, powder, capsule, or liquid form such as solution, suspension, syrup, emulsion, lemonade, lotion and the like.

If needed, there may be included in the above preparations auxiliary substances, stabilizing agents, wetting agents and other commonly used additives such as lactose, citric acid, tartaric acid, stearic acid, magnesium stearate, terra alba, sucrose, corn starch, talc, gelatin, agar, pectin, peanut oil, olive oil, cacao butter, ethylene glycol, and the like.

While the dosage of the compound (I) may vary from and also depend upon the age, conditions of the patient, a kind of diseases or conditions, a kind of the compound (I) to be applied, etc. In general amounts between 0.01 mg and about 500 mg or even more per day may be administered to a patient. An average single dose of about 0.05 mg, 0.1 mg, 0.25 mg, 0.5 mg, 1 mg, 20 mg, 50 mg, 100 mg of the object compound (I) of the present invention may be used in treating diseases.

The following Preparations and Example are given for the purpose of illustrating the present invention.

PREPARATION 1

To a solution of 3-indolebutyric acid (25 g) and potassium carbonate (20 g) in dimethylformamide (150 ml) was added benzylbromide (21 g) at room temperature. After stirring for 4 hours, the mixture was poured into ice and diluted hydrochloric acid (300 ml). The organic layer was extracted with ethyl acetate (150 ml), and the extract was washed with water (150 ml×3) and dried over magnesium sulfate. After the solvent was removed in vacuo, the residue was crystallized from n-hexane to give a solid of benzyl 4-(3-indolyl)butyrate (33.9 g).

mp: 55° C.

NMR (CDCl$_3$, δ): 2.10 (2H, m), 2.43 (2H, t, J=7.5 Hz), 2.70 (2H, t, J=7.5 Hz), 5.10 (2H, s), 6.90 (1H, d, J=2 Hz), 7.10 (1H, dt, J=2 Hz, 8 Hz), 7.16 (1H, dt, J=2 Hz, 7 Hz), 7.30 (1H, m), 7.33 (5H, s), 7.58 (1H, d, J=8 Hz), 7.9 (1H, br s).

PREPARATION 2

To a solution of benzyl 4-(3-indolyl)butyrate (33.70 g) in dichloromethane (400 ml) were added triethylamine (30 ml), 4-dimethylaminopyridine (1.22 g) and 3-nitrobenzoyl chloride (30.0 g). After refluxed for 16 hours, 3-nitrobenzoyl chloride (10.5 g) and triethylamine (5 ml) were added to the mixture. The mixture was allowed to reflux for 19 hours and 3-dimethylaminopropylamine (15 ml) was added at 0° C. The mixture was washed with diluted hydrochloric acid (200 ml ×2) and water (200 ml×4) and dried over magnesium sulfate. The solvent was removed in vacuo to give a solid of benzyl 4-[1-(3-nitrobenzoyl)indol-3-yl]butyrate (47.61 g).

mp: 89° C.

IR (CDCl$_3$, δ): 2.00 (2H, m), 2.40 (2H, t, J=7.5 Hz), 2.70 (2H, t, J=7.5 Hz), 5.06 (2H, s), 6.93 (1H, s), 7.30 (5H, s), 7.35 (1H, m), 7.40 (1H, dt, J=2 Hz, 8 Hz), 7.60 (1H, dd, J=2 Hz, 8 Hz), 7.72 (1H, t, J=8 Hz), 8.05 (1H, dd, J=2 Hz, 8 Hz), 8.38 (1H, d, J=8 Hz), 8.48 (1H, m), 8.60 (1H, m)

PREPARATION 3

Benzyl 4-[1-(3-nitrobenzoyl)indol-3-yl]butyrate (47.31 g) was subjected to hydrogenation with 10% palladium on carbon in a mixture of 1,4-dioxane (500 ml) and methanol (500 ml) for 17 hours. After the catalyst was filtered off, the filtrate was evaporated in vacuo. To the residue was added 1N-hydrochloric acid (120 ml) to give 4-[1-(3-aminobenzoyl)indol-3-yl]butyric acid hydrochloride (34.75 g).

mp: 181°-183° C.

NMR (CDCl$_3$+CD$_3$OD, δ): 2.00 (2H, m), 2.37 (2H, t, J=7.5 Hz), 2.70 (2H, t, J=7.5 Hz), 7.00 (1H, s), 7.35 (3H, m), 7.5-7.8 (4H, m), 8.35 (1H, dt, J=2 Hz, 8 Hz).

PREPARATION 4

To a mixture of nitric acid (d=1.42:20 ml) and sulfuric acid (d=1.84:20 ml) was added 2,3-dimethyl benzoic acid (6.0 g) at 0° C. After stirring for 3 hours, the mixture was poured into ice water (300 ml). The organic layer was extracted with ethyl acetate (100 ml) and washed with water (100 ml×3). The solution was dried over magnesium sulfate and the solvent was removed in vacuo. The residue was purified by a column of silica gel to give a yellow solid of 2,3-dimethyl-5-nitrobenzoic acid (1.80 g).

NMR (CDCl$_3$+CD$_3$OD, δ): 2.43 (3H, s), 2.58 (3H, s), 8.14 (1H, d, J=2 Hz), 8.56 (1H, d, J=2 Hz).

PREPARATION 5

To a solution of 2,3-dimethyl-5-nitrobenzoic acid (1.7 g) in dichloromethane (20 ml) was added oxalylchloride (1.0 ml) and dimethylformamide (0.05 ml). After the solution was stirred for 1 hour at room temperature, the solvent was removed in vacuo. The residue was dissolved in tetrahydrofuran (20 ml). To the solution was added a solution of sodium phenolate (20 mmol) in tetrahydrofuran (20 ml) at 0° C. The mixture was stirred for 30 minutes and poured into diluted hydrochloric acid (110 ml). The organic layer was extracted with ethyl acetate (50 ml) and washed with water (50 ml×3). The solution was dried over magnesium sulfate and the solvent was removed in vacuo. The residue was purified by a column of silica gel to give a yellow solid of 2,3-dimethyl-5-nitrobenzoic acid phenyl ester (1.50 g).

NMR (CDCl$_3$, δ): 2.48 (3H, s), 2.65 (3H, s), 7.2-7.6 (5H, m), 8.23 (1H, d, J=2 Hz), 8.78 (1H, d, J=2 Hz).

PREPARATION 6

To a solution of 4,4'-dichlorobenzophenone (2.51 g) in isopropyl alcohol (15 ml) was added sodium borohydride (0.45 g). The mixture was stirred for 4 hours at 50° C. and poured into diluted hydrochloric acid (60 ml). The organic layer was extracted with ethyl acetate (20 ml) and washed with water (30 ml×2). The solution was dried over magnesium sulfate. The solvent was removed in vacuo to give colorless oil of bis(4-chlorophenyl)methanol (2.50 g).

NMR (CDCl$_3$, δ): 5.70 (1H, s), 7.2-7.4 (8H, m).

PREPARATION 7

To a solution of bis(4-chlorophenyl)methanol (2.0 g) in dichloromethane (20 ml) was added oxalylchloride (1 ml). The mixture was stirred for 4 hours and the solvent was removed in vacuo. The residue was dissolved in n-hexane (20 ml) and filtered off. The solvent was removed in vacuo to give colorless oil of bis(4-chlorophenyl)methyl chloride (2.15 g).

NMR (CDCl$_3$, δ): 6.06 (1H, s), 7.32 (8H, s)

PREPARATION 8

A mixture of methyl 3-(chloroformyl)propionate (3 ml) and aluminum chloride [6.50 g] in dichloromethane (40 ml) was stirred at 20° C. for 1 hour. A solution of 2-methylindole (3 g) in dichloromethane (20 ml) was added to the mixture at 20° C. and the resulting mixture was stirred at 20° C. for 1 hour. The reaction mixture was poured into a mixture of ethyl acetate and 1N hydrochloric acid. The organic layer was separated, washed with water and brine, and dried over magnesium sulfate. After evaporation of solvent, the residue was purified by column chromatography on silica gel (100 g) eluting with chloroform and with recrystallization from a mixture of ethyl acetate and hexane to give methyl 4-(2-methylindol-3-yl)-4-oxobutyrate (908 mg) as pale brown crystals.

mp: 145°–147° C.

NMR (CDCl$_3$ and CD$_3$OD, δ): 2.65 (3H, s), 2.80 (2H, t, J=7.5 Hz), 3.30 (2H, t, J=7.5 Hz), 3.72 (3H, s), 7.10–7.38 (3H, m), 7.92–8.08 (1H, m).

PREPARATION 9

The following compounds were obtained according to a similar manner to that of Preparation 8.

(1) Methyl 4-(5-chloroindol-3-yl)-4-oxobutyrate mp: 150°–153° C.

NMR (CDCl$_3$—CD$_3$OD, δ): 2.28 (2H, t, J=7.5 Hz), 3.24 (2H, t, J=7.5 Hz), 3.72 (3H, s), 7.20 (1H, dd, J=1.5, 8 Hz), 7.30–7.42 (2H, m), 8.00 (1H, d, J=1.5 Hz), 8.32 (1H, s).

(2) Methyl 5-(3-indolyl)-5-oxovalerate mp: 183° C.

NMR (DMSO-d$_6$, δ): 1.90 (2H, t, J=7.5 Hz), 2.40 (2H, t, J=7.5 Hz), 2.90 (2H, t, J=7.5 Hz), 3.60 (3H, s), 7.1–7.3 (2H, m), 7.4–7.5 (1H, m), 8.1–8.2 (1H, m), 8.30 (1H, d, J=3 Hz).

(3) Methyl 6-(3-indolyl)-6-oxohexanoate mp: 130° C.

NMR (CDCl$_3$, δ): 1.64 (4H, m), 2.36 (2H, t, J=7 Hz), 2.87 (2H, t, J=7 Hz), 3.59 (3H, s), 7.1–7.3 (2H, m), 7.4–7.5 (1H, m), 8.2–8.4 (1H, m), 8.33 (1H, s).

PREPARATION 10

To a solution of methyl 4-(2-methylindol-3-yl)-4-oxobutyrate (2.0 g) in tetrahydrofuran (50 ml) was added a 1M solution of boran in tetrahydrofuran (16.5 ml) at 0° C. After stirred at 0° C. for 30 minutes, the mixture was poured into a mixture of ethyl acetate and brine. The organic layer was separated, washed with water and brine, and dried over magnesium sulfate. After evaporation of solvent, the residue was purified by column chromatography on silica gel (50 g) eluting with chloroform to give methyl 4-(2-methylindol-3-yl)butyrate (1.67 g) as a yellow oil.

NMR CDCl$_3$, δ): 1.85–2.09 (2H, m), 2.25–2.40 (5H, m), 2.72 (2H, t, J=7.5 Hz), 3.60 (3H, s), 7.00–7.15 (2H, m), 7.15–7.29 (1H, m), 7.45–7.53 (1H, m), 7.75 (1H, broad s).

PREPARATION 11

Boron trifluoride etherate (4.2 ml) was added to a mixture of methyl 4-(5-chloroindol-3-yl)-4-oxobutyrate (3.00 g) and sodium borohydride (0.855 g) in tetrahydrofuran (100 ml) at 25° C. over 20 minutes. After the mixture was stirred at 25° C. for 3 hours, acetone (5 ml) was added. The reaction mixture was poured into a mixture of ethyl acetate and 1N hydrochloric acid. The organic layer was separated, washed with water and brine, and dried over magnesium sulfate. After evaporation of solvent, the residue was purified by column chromatography on silica gel (200 ml) eluting with chloroform and by recrystallization from a mixture of ethyl acetate and hexane to give methyl 4-(5-chloroindol-3-yl)butyrate (989 mg) as colorless crystals.

mp: 74°–75° C.

NMR (CDCl$_3$, δ): 1.93°–2.13 (2H, m), 2.39 (2H, t, J=7.5 Hz), 2.76 (2H, t, J=7.5 Hz), 3.68 (3H, s), 7.00 (1H, d, J=2.5 Hz), 7.13 (1H, dd, J=8, 2.5 Hz), 7.28 (1H, d, J=8 Hz), 7.55 (1H, d, J=2.5 Hz), 8.01 (1H, broad s).

PREPARATION 12

The following compounds were obtained according to a similar manner to that of Preparation 11.

(1) Methyl 5-(3-indolyl)valerate mp: 56°–57° C.

NMR (CDCl$_3$, δ): 1.7–1.8 (4H, m), 2.3–2.5 (2H, m), 2.7–2.9 (2H, m), 6.98 (1H, m), 7.0–7.3 (2H, m), 7.35 (1H, dd, J=2, 7.5 Hz), 7.59 (1H, d, J=7.5 Hz), 7.93 (1H, broad s).

(2) Methyl 6-(3-indolyl)hexanoate mp: 89° C.

NMR (CDCl$_3$, δ): 1.3–1.5 (2H, m), 1.6–1.9 (4H, m), 2.32 (2H, t, J=7.5 Hz), 2.76 (2H, t, J=7.5 Hz), 6.96 (1H, s), 7.0–7.3 (2H, m), 7.35 (1H, d, J=7.5 Hz), 7.60 (1H, d, J=7.5 Hz), 7.92 (1H, broad s).

PREPARATION 13

To a solution of methyl 4-(2-methylindol-3-yl)-butyrate (1.65 g) in methanol (50 ml) was added 1N aqueous sodium hydroxide (18 ml) at 20° C. and the mixture was stirred at 20° C. for 3 hours. After evaporation of the solvent, the residue was poured into a mixture of ethyl acetate and 1N hydrochloric acid. The organic layer was separated, washed with water and brine, and dried over magnesium sulfate. After evaporation of solvent, the crystalline residue was washed with hexane to give 4(2-methylindol-3-yl)butyric acid (1.23 g) as reddish brown crystals.

mp: 85°–87° C.

CDCl$_3$, δ): 1.85–2.10 (2H, m), 2.28–2.45 (5H, m), 2.76 (2H, t, J=7.5 Hz), 7.00–7.18 (2H, m), 7.18–7.30 (1H, m), 7.40–7.54 (1H, m), 7.70 (1H, broad s).

PREPARATION 14

The following compounds were obtained according to a similar manner to that of Preparation 13.

(1) 4-(5-Chloroindol-3-yl)butyric acid mp: 139°–141° C.

NMR (CDCl$_3$—CD$_3$OD, δ): 1.98–2.14 (2H, m), 2.40 (2H, t, J=7.5 Hz), 2.89 (2H, t, J=7.5 Hz), 7.04 (1H, s), 7.13 (1H, dd, J=2.5, 10 Hz), 7.28 (1H, d, J=10 Hz), 7.56 (1H, d, J=2.5 Hz).

(2) 5-(3-Indolyl)valeric acid mp: 105° C.

NMR (CDCl$_3$, δ): 1.7–1.9 (4H, m), 2.40 (2H, t, J=7.5 Hz), 2.80 (2H, t, J=7.5 Hz), 6.95 (1H, m), 7.0–7.3 (2H, m), 7.34 (1H, m), 7.60 (1H, m), 7.91 (1H, broad s).

(3) 6-(3-Indolyl)hexanoic acid mp: 142° C.

NMR (CDCl$_3$—CD$_3$OD, δ): 1.3–1.5 (2H, m), 1.5–1.8 (4H, m), 2.26 (2H, t, J=7.5 Hz), 2.73 (2H, t, J=7.5 Hz), 6.95 (1H, s), 7.0–7.2 (2H, m), 7.32 (1H, d, J=7.5 Hz), 7.52 (1H, d, J=7.5 Hz).

PREPARATION 15

A mixture of 4-(5-chloroindol-3-yl)butyric acid (1.50 g), benzyl bromide (1.10 g) and potassium carbonate (0.987 g) in N,N-dimethylformamide (12 ml) was stirred at 25° C. for 4.5 hours. The mixture was poured into a mixture of ethyl acetate and 1N hydrochloric acid. The organic layer was separated, washed with water and brine, and dried over magnesium sulfate. After evaporation of solvent, the residue was chromatographed on silica gel (40 g) eluting with a mixture of hexane and ethyl acetate (10:1) to give benzyl 4-(5-chloroindol-3-yl)butyrate (1.40 g) as pale yellow crystals.

mp: 46°–47° C.

NMR (CDCl$_3$, $\delta$): 1.92–2.18 (2H, m), 2.44 (2H, t, J=7.5 Hz), 2.76 (2H, t, J=7.5 Hz), 5.14 (2H, s), 6.98 (1H, s), 7.14 (1H, d, J=10 Hz), 7.21–7.51 (6H, m), 7.53 (1H, s), 7.95 (1H, broad s).

PREPARATION 15

The following compounds were obtained according to a similar manner to that of Preparation 15.

(1) Benzyl 2-(3-indolyl)acetate mp: 69°–70° C.

NMR (CDCl$_3$, $\delta$): 3.84 (2H, s), 5.15 (2H, s), 7.0–7.3 (3H, m), 7.32 (5H, s), 7.3–7.4 (1H, m), 7.60 (1H, d, J=7.5 Hz), 8.08 (1H, broad s).

(2) Benzyl 3-(3-indolyl)propionate mp: 69°–70° C.

NMR (CDCl$_3$, $\delta$): 2.5–2.6 (2H, m), 2.8–3.0 (2H m), 4.87 (2H, s), 6.72 (1H, m), 6.8–7.0 (2H, m), 7.0–7.2 (5H, m), 7.3–7.5 (2H, m).

(3) Benzyl 5-(3-indolyl)valerate mp: 76° C.

NMR (CDCl$_3$, $\delta$): 1.7–1.8 (4H, m), 2.3–2.5 (2H, m), 2.7–2.8 (2H, m), 5.10 (2H, s), 6.95 (1H, m), 7.0–7.3 (2H, m), 7.33 (5H, s), 7.58 (1H, m), 7.90 (1H, broad s).

(4) Benzyl 6-(3-indolyl)hexanoate mp: 72° C.

CDCl$_3$, $\delta$): 1.3–1.5 (2H, m), 1.6–1.8 (4H, m), 2.37 (2H, t, J=9.5 Hz), 2.75 (2H, t, J=7.5 Hz), 5.10 (2H, s), 6.95 (1H, d, J=2 Hz), 7.0–7.3 (2H, m), 7.3–7.4 (6H, m), 7.59 (1H, dd, J=2, 7.5 Hz), 7.90 (1H, broad s).

PREPARATION 17

A solution of 4-(2-methylindol-3-yl)butyric acid (600 mg) in N,N-dimethylformamide (10 ml) was added to a suspension of sodium hydride (60% dispersion in mineral oil, 243 mg) in N,N-dimethylformamide (5 ml) at 20° C. and the mixture was stirred at 20° C. for 1 hour. A solution of phenyl 3-nitrobenzoate (671 mg) in tetrahydrofuran (10 ml) was added to the mixture at −35° C. and the resulting mixture was stirred at the same temperature for 2 hours. The mixture was poured into a mixture of ethyl acetate and 1N hydrochloric acid. The organic layer was separated, washed with water and brine, and dried over magnesium sulfate. After evaporation of solvent, the residue was chromatographed on a silica gel (25 g) column with a mixture of hexane and ethyl acetate (10:1 to 1:1) to give 4-[2-methyl-1-(3-nitrobenzoyl)indol-3-yl]butyric acid (749 mg) as yellow crystals.

mp: 158°–160° C.

NMR (CDCl$_3$—CD$_3$OD, $\delta$): 1.85–2.06 (2H, m), 2.26–2.50 (5H, m), 2.75 (2H, t, J=7.5 Hz), 6.92 (1H, d, J=8 Hz), 7.04 (1H, dt, J=8, 1.5 Hz), 7.20 (1H, dt, J=8, 1.5 Hz), 7.52 (1H, d, J=8 Hz), 7.72 (1H, t, J=8 Hz), 8.03 (1H, dif-dd, J=8 Hz), 8.50 (1H, dif-dd, J=8 Hz), 8.58 (1H, dif-d).

PREPARATION 18

The following compounds were obtained according to a similar manner to that of Preparation 17.

(1) 4-[1-(4-Nitrobenzoyl)indol-3-yl]butyric acid

NMR (CDCl$_3$, $\delta$): 2.1–1.9 (2H, m), 2.42 (2H, t, J=7.5 Hz), 2.73 (2H, t, J=7.5 Hz), 6.95 (1H, s), 7.3–7.5 (2H, m), 7.60 (1H, m), 7.82 (2H, d, J=10 Hz), 8.35 (3H, m).

(2) 4-[1-(2,3-Dimethyl-5-nitrobenzoyl)indol-3-yl]butyric acid

NMR (CDCl$_3$, $\delta$): 1.9–2.1 (2H, m), 2.32 (3H, s), 2.42 (2H, t, 7.5 Hz), 2.50 (3H, s), 2.70 (2H, t, J=7.5 Hz), 6.70 (1H, br s), 7.3–7.7 (3H, m), 8.12 (1H, d, J=2 Hz), 8.20 (1H, d, J=2 Hz), 8.5 (1H, br s).

PREPARATION 19

To a suspension of sodium hydride (60% dispersion in mineral oil) (0.59 g) in N,N-dimethylformamide (10 ml) was added a solution of 4-(3-indolyl)butyric acid (1.0 g) in N,N-dimethylformamide (5 ml). The mixture was stirred at room temperature for 30 minutes and cooled at −40° C. To the mixture was added a solution of 3-nitrobenzyl bromide (1.06 g) in N,N-dimethylformamide (5 ml). The mixture was stirred at −40° C. for 20 minutes and partitioned between ethyl acetate and 7% hydrochloric acid. The organic layer was washed with water, dried over magnesium sulfate and evaporated. The residue was washed with diisopropyl ether to give 4-[1-(3-nitrobenzyl)indol-3-yl]butyric acid as a white powder (1.20 g).

mp: 121° C.

NMR (CDCl$_3$, $\delta$): 1.9–2.2 (2H, m), 2.40 (2H, t, J=7.5 Hz), 2.85 (2H, t, J=7.5 Hz), 5.39 (2H, s), 7.00 (1H, s), 7.1–7.3 (3H, m), 7.3–7.4 (1H, m), 7.46 (1H, t, J=7.5 Hz), 7.64 (1H, d, J=7.5 Hz), 8.03 (1H, s), 8.11 (1H, d, J=7.5 Hz).

PREPARATION 20

The following compounds were obtained according to a similar manner to that of Preparation 2.

(1) Benzyl 4-[5-chloro-1-(3-nitrobenzoyl)indol-3-yl]butyrate mp: 134°–135° C.

NMR (CDCl$_3$, $\delta$): 1.93 (2H, m), 2.45 (2H, t, J=7.5 Hz), 2.72 (2H, t, J=7.5 Hz), 5.11 (2H, s), 6.99 (1H, s), 7.30–7.50 (6H, m), 7.56 (1H, d, J=2.5 Hz), 7.78 (1H, t, J=8 Hz), 8.08 (1H, dif-dd, J=8 Hz), 8.37 (1H, d, J=8 Hz), 8.50 (1H, dif-dd, J=8 Hz), 8.60 (1H, dif-d).

(2) Benzyl 2-[1-(3-nitrobenzoyl)indol-3-yl]acetate mp: 126° C.

NMR (CDCl$_3$, $\delta$): 3.78 (2H, s), 5.15 (2H, s), 7.20 (1H, s), 7.30 (5H, s), 7.2–7.5 (2H, m), 7.5–7.6 (1H, m), 7.74 (1H, t, J=7.5 Hz), 8.0–8.1 (1H, m), 8.4–8.5 (2H, m), 8.6 (1H, m).

(3) Benzyl 3-[1-(3-nitrobenzoyl)indol-3-yl]propionate mp: 125° C.

NMR (CDCl$_3$, $\delta$): 2.75 (2H, t, J=7.5 Hz), 3.07 (2H, t, J=7.5 Hz), 5.10 (2H, s), 6.96 (1H, s), 7.2–7.5 (7H, m), 7.6 (1H, m), 7.72 (1H, t, J=7.5 Hz), 7.9–8.0 (1H, m), 8.4–8.6 (3H, m).

(4) Benzyl 5-[1-(3-nitrobenzoyl)indol-3-yl]valerate mp: 102°–103° C.

CDCl$_3$, $\delta$): 1.6–1.9 (4H, m), 2.3–2.5 (2H, m), 2.6–2.8 (2H, m), 5.08 (2H, s), 6.95 (1H, s), 7.33 (5H, s), 7.3–7.5

(2H, m), 7.56 (1H, m), 7.75 (1H, t, J=7.5 Hz), 8.06 (1H, m), 8.39 (1H, m), 8.46 (1H, m), 8.60 (1H, m).

(5) Benzyl 6-[1-(3-nitrobenzoyl)indol-3-yl]hexanoate
mp: 85° C.

NMR (CDCl$_3$, δ): 1.3–1.5 (2H, m), 1.6–1.8 (4H, m), 2.36 (2H, t, J=7.5 Hz), 2.67 (2H, t, J=7.5 Hz), 5.10 (2H, s), 6.92 (1H, s), 7.33 (5H, s), 7.3–7.5 (2H, m), 7.76 (1H, t, J=7.5 Hz), 8.05 (1H, dt, J=7.5, 2 Hz), 8.38 (1H, dd, J=7.5, 2 Hz), 8.46 (1H, dt, J=7.5, 2 Hz), 8.60 (1H, t, J=2 Hz).

(6) Benzyl 4-[1-(3-nitrobenzenesulfonyl)indol-3-yl]butyrate

NMR (CDCl$_3$, δ): 1.9–2.1 (2H, m), 2.40 (2H, t, J=7.5 Hz), 2.70 (2H, t, J=7.5 Hz), 5.11 (2H, s), 7.2–7.5 (9H, m), 7.60 (1H, t, J=7.5 Hz), 8.00 (1H, d, J=7.5 Hz), 8.13 (1H, m), 8.33 (1H, m), 8.68 (1H, m).

PREPARATION 21

To a solution of benzyl 4-[1-(3-nitrobenzenesulfonyl)indol-3-yl]butyrate (1.95 g) in 1,4-dioxane (15 ml) was added 1N-sodium hydroxide (8 ml). The mixture was stirred for 2 hours and poured into diluted hydrochloric acid. The organic layer was extracted with ethyl acetate (30 ml) and washed with water (30 ml×3). The solution was dried over magnesium sulfate and the solvent was removed in vacuo. The residue was crystallized with diisopropyl ether to give a yellow solid of 4-[1-[3-nitrobenzenesulfonyl)indol-3-yl]butyric acid (1.45 g).

NMR (DMSO-d$_6$, δ): 1.7–2.0 (2H, m), 2.25 (2H, t, J=7.5 Hz), 2.67 (2H, t, 7.5 Hz), 7.2–7.5 (2H, m), 7.65 (1H, d, J=7.5 Hz), 7.70 (1H, s), 7.88 (1H, t, J=7.5 Hz), 8.00 (1H, d, J=7.5 Hz), 8.40 (1H, m), 8.50 (1H, m), 8.62 (1H, m).

PREPARATION 22

To a solution of 4-[1-(3-nitrobenzenesulfonyl)indol-3-yl]butyric acid (1.0 g) in 1,4-dioxane (15 ml) and methanol (15 ml) was added 10% palladium on carbon (0.93 g). The mixture was hydrogenolized for 8 hours at room temperature. The catalyst was filtered off and the solvent was removed in vacuo. The residue was purified by a column of silica gel to give a yellow solid of 4-[1-(3-aminobenzenesulfonyl)indol-3-yl]butyric acid (0.13 g).

NMR (DMSO-d$_6$, δ): 1.7–2.0 (2H, m), 2.22 (2H, t, J=7.5 Hz), 2.68 (2H, t, J=7.5 Hz), 6.75 (1H, dd, J=7.5, 2 Hz), 6.9–7.4 (5H, m), 7.45 (1H, s), 7.60 (1H, d, J=7.5 Hz), 7.83 (1H, d, J=7.5 Hz).

PREPARATION 23

The following compound was obtained according to a similar manner to that of Preparation 22.
4-[1-(5-Amino-2,3-dimethylbenzoyl)indol-3-yl]butyric acid NMR (DMSO-d$_6$, δ): 1.9–2.1 (2H, m), 2.20 (3H, s), 2.32 (2H, t, J=7.5 Hz), 2.40 (3H, s), 2.70 (2H, t, J=7.5 Hz), 6.70 (1H, br s), 7.2–7.7 (5H, m), 8.40 (1H, br s).

PREPARATION 24

To a solution of benzyl 4-[5-chloro-1-(3-nitrobenzoyl)indol-3-yl]butyrate (1.3 g) in a mixture of methanol (35 ml), 1,4-dioxane (35 ml) and water (5 ml) was added 10% palladium on activated carbon (400 mg), and the mixture was stirred under hydrogen atmosphere (3 atm) at 20° C. for 4 hours. The catalyst was filtered off and the filtrate was evaporated. The residue was chromatographed on silica gel (40 g) eluting with 2% methanol in chloroform to give 4-[1-(3-aminobenzoyl)-5-chloroindol-3-yl]butyric acid (731 mg) as pale yellow crystals.
mp: 139°–143° C.

NMR (CDCl$_3$—CD$_3$OD, δ): 1.88–2.15 (2H, m), 2.49 (2H, t, J=7.5 Hz), 2.73 (2H, t, J=7.5 Hz), 6.90–7.22 (4H, m), 7.22–7.42 (2H, m), 7.52 (1H, d, J=2.5 Hz), 8.30 (1H, d, J=8 Hz).

PREPARATION 25

The following compounds were obtained according to a similar manner to that of Preparation 24.
(1) 5-[1-[3-Aminobenzoyl)indol-3-yl]valeric acid
mp: 117°–118° C.

NMR (CDCl$_3$, δ): 1.6–1.9 (4H, m), 2.3–2.5 (2H, m), 2.6–2.8 (2H, m), 6.9 (1H, m), 7.0–7.2 (3H, m), 7.3–7.5 (3H, m), 7.54 (1H, m), 8.39 (1H, m).

(2) 2-[1-(3-Aminobenzoyl)indol-3-yl]acetic acid

NMR (CDCl$_3$—CD$_3$OD, δ): 3.70 (2H, s), 6.9 (1H, m), 7.0–7.1 (2H, m), 7.3–7.5 (4H, m), 7.6 (1H, m), 8.4 (1H, m).

(3) 3-[1-(3-Aminobenzoyl)indol-3-yl]propionic acid
mp: 148° C.

NMR (CD$_3$OD—CDCl$_3$, δ): 2.74 (2H, t, J=7.5 Hz), 3.02 (2H, t, J=7.5 Hz), 6.8–6.9 (1H, m), 6.9–7.0 (1H, m), 7.0–7.1 (1H, m), 7.1–7.5 (4H, m), 7.5–7.6 (1H, m), 8.3–8.4 (1H, m).

(4) 6-[1-(3-Aminobenzoyl)indol-3-yl]hexanoic acid

NMR (CDCl$_3$, δ): 1.3–1.5 (2H, m), 1.5–1.8 (4H, m), 2.36 (2H, t, J=7.5 Hz), 2.70 (2H, t, J=7.5 Hz), 6.96 (1H, d, J=7.5 Hz), 7.06 (1H, s), 7.15 (1H, d, J=7.5 Hz), 7.0–7.5 (4H, m), 7.54 (1H, dd, J=7.5, 2 Hz), 8.40 (1H, dd, J=7.5, 2 Hz).

PREPARATION 26

To a solution of 4-[2-methyl-1-(3-nitrobenzoyl)indol-3-yl]butyric acid (600 mg) in a mixture of methanol (30 ml) and 1,4-dioxane (30 ml) was added 10% palladium on activated carbon (300 mg), and the mixture was stirred under hydrogen atmosphere (3 atm) at 20° C. for 45 minutes. The catalyst was filtered off and the filtrate was evaporated. The residue was chromatographed on a silica gel column (25 ml) eluting with a mixture of chloroform and methanol (10:1) to give 4-[1-(3-aminobenzoyl)-2-methylindol-3-yl]butyric acid (490 mg) as a yellow foam.

NMR CDCl$_3$—CD$_3$OD, δ): 1.85–2.10 (2H, m), 2.25–2.47 (5H, m), 2.75 (2H, t, J=7.5 Hz), 6.85–7.35 (7H, m), 7.49 (1H, d, J=8 Hz).

PREPARATION 27

The following compounds were obtained according to a similar manner to that of Preparation 26.
(1) 4-[1-(4-Aminobenzoyl)indol-3-yl]butyric acid NMR (CDCl$_3$, δ): 1.9–2.1 (2H, m), 2.38 (2H, t, J=7.5 Hz), 2.75 (2H, t, J=7.5 Hz), 6.75 (2H, d, J=8 Hz), 7.20 (1H, s), 7.4–7.2 (2H, m), 7.7–7.5 (3H, m), 8.30 (1H, dd, J=1 Hz, 8 Hz).

(2) 4-[1-(3-Aminobenzyl)indol-3-yl]butyric acid
mp: 135° C.

NMR (CD$_3$OD, δ): 1.99 (2H, m), 2.35 (2H, t, J=7.5 Hz), 2.80 (2H, t, J=7.5 Hz), 6.4–6.7 (3H, m), 6.9–7.2 (4H, m), 7.25 (1H, m), 7.54 (1H, m).

EXAMPLE 1

To a solution of 4-[1-(3-aminobenzoyl)indol-3-yl]butyric acid hydrochloride (14.5 g) and diisopropylethylamine (22 ml) in dichloromethane (300 ml) was added bis(4-isobutylphenyl)methyl bromide (14.5 g) at room temperature. After stirring for 15 hours, diisopropylethylamine (7 ml) and bis(4-isobutylphenyl)methyl bromide 2.0 g) were added to the mixture. The mixture was stirred for 6 hours at room temperature and acidified by 7% hydrochloric acid (50 ml). The separated organic layer was washed with water and dried over magnesium sulfate. After the solvent was removed in vacuo, the residue was chromatographed on a column of silica gel (200 g) and eluted with chloroform to give a solid of 4-[1-[3-[bis(4-isobutylphenyl)methylamino]benzoyl]indol-3-yl]butyric acid (23.15 g).

mp: 74.76° C.

NMR (CDCl₃, δ): 0.87 (12H, d, J=7.5 Hz), 1.80 (2H, m), 2.00 (2H, m) 2.40 (2H, m), 2.43 (4H, d, J=7.5 Hz), 2.70 (2H, t, J=7.5 Hz), 5.50 (1H, s), 6.70 (1H, dd, J=2 Hz, 8 Hz), 6.90 (1H, s), 6.95 (1H, d, J=8 Hz), 7.10 (5H, m), 7.1-7.4 (7H, m), 7.55 (1H, dd, J=2 Hz, 8 Hz), 8.35 (1H, d, J=8 Hz).

EXAMPLE 2

A mixture of 4-[1-(3-aminobenzoyl)-2-methylindol-3-yl]butyric acid (587 mg), bis(4-isobutylphenyl)methyl chloride (905 mg) and diisopropylethylamine (754 mg) in dichloromethane (20 ml) was stirred at 20° C. for 14 hours. The reaction mixture was poured into a mixture of ethyl acetate and 1N hydrochloric acid. The organic layer was separated, washed with water and brine, and dried over magnesium sulfate. After evaporation of the solvent, the residue was chromatographed on a silica gel column (50 ml) eluting with a mixture of chloroform and methanol (50:1) to give 4-[1-[3-[bis(4-isobutylphenyl)methylamino]benzoyl]-2-methylindol-3-yl]butyric acid (720 mg).

NMR (CDCl₃, δ): 0.75 (12H, d, J=7.5 Hz), 1.65-2.06 (4H. m), 2.25 (3H, s), 2.32-2.50 (6H, m), 2.75 (2H, t, J=7.5 Hz), 5.48 (1H, s), 6.75-7.30 (15H, m), 7.45 (1H, d, J=8 Hz).

EXAMPLE 3

The following compounds were obtained according to a similar manner to that of Example 2.

(1) 4-[1-[3-[Bis(3-isobutylphenyl)methylamino]benzoyl]indol-3-yl]butyric acid

NMR (CDCl₃, δ): 0.81 (1H, d, J=7.5 Hz), 1.62-2.12 (4H, m), 2.30-2.50 (6H, m), 2.70 (2H, t, J=7.5 Hz), 5.50 (1H, s), 6.74-6.90 (1H, m), 6.90-7.46 (14H, m), 7.48-7.60 (1H, m), 8.35 (1H, d, J=8 Hz).

(2) 4-[1-[5-[Bis(4-isobutylphenyl)methylamino]-2,3-dimethylbenzoyl]indol-3-yl]butyric acid NMR (CDCl₃, δ): 0.85 (12H, d, J=7.5 Hz), 1.7-2.0 (2H, m), 1.9-2.1 (2H, m), 2.02 (3H, s), 2.17 (3H, s), 2.3-2.5 (6H, m), 2.6-2.8 (2H, m), 5.42 (1H, s), 6.40 (1H, s), 6.80 (1H, br s), 7.0-7.4 (13H, m), 7.5-7.6 (1H, m).

(3) 4-[1-[3-[Bis(4-isobutylphenyl)methylamino]benzenesulfonyl]indol-3-yl]butyric acid NMR (CDCl₃, δ): 0.90 (12H, d, J=7.5 Hz), 1.7-2.0 (2H, m), 2.0-2.1 (2H, m), 2.40 (2H, t, J=7.5 Hz), 2.45 (4H, d, J=7.5 Hz), 2.73 (2H, t, J=7.5 Hz), 5.32 (1H, s), 6.5-6.7 (1H, m), 7.0-7.3 (14H, m), 7.4-7.5 (1H, m), 7.8-7.9 (1H, m).

EXAMPLE 4

To a solution of 4-[1-(3-aminobenzoyl)indol-3-yl]butyric acid (1.0 g) and diisopropylethylamine (1.3 g) in carbon tetrachloride (20 ml) was added bis(4-chlorophenyl)methyl chloride (0.84 g). The mixture was refluxed for 6 hours and the solvent was removed in vacuo. The residue was dissolved in ethyl acetate (20 ml) and diluted hydrochloric acid (30 ml) and washed with water (30 ml×3). The solution was dried over magnesium sulfate and the solvent was removed in vacuo. The residue was purified by a column of silica gel to give a yellow solid of 4-[1-[3-[bis(4-chlorophenyl)methylamino]benzoyl]indol-3-yl]butyric acid (1.19 g).

NMR (CDCl₃, δ): 1.9-2.1 (2H, m), 2.45 (2H, t, J=7.5 Hz), 2.68 (2H, t, 7.5 Hz), 5.50 (1H, s), 6.70 (1H, dd, J=7.5, 2.5 Hz), 6.85 (1H, m), 7.00 (1H, s), 7.02 (1H, d, J=7.5 Hz), 7.2-7.4 (1H, m), 7.5-7.6 (1H, m), 8.35 (1H, dd, J=7.5, 2.5 Hz).

EXAMPLE 5

A mixture of 4-[1-(3-aminobenzoyl)-5-chloroindol-3-yl]butyric acid (700 mg), bis(4-isobutylphenyl)methyl bromide (705 mg) and diisopropylethylamine (620 mg) in dichloromethane (20 ml) was stirred at 20° C. for 1 hour, and then bis(4-isobutylphenyl)methyl bromide (150 mg) and diisopropylethylamine (70 mg) were added. After stirred at 20° C. for 3 hours, the reaction mixture was poured into iced 1N hydrochloric acid. The organic layer was separated, washed with water and brine, and dried over magnesium sulfate. After evaporation of the solvent, the residue was chromatographed on silica gel (20 g) eluting with a mixture of hexane and ethyl acetate (10:1 to 1:1) to give 4-[1-[3-[bis(4-isobutylphenyl)methylamino]benzoyl]-5-chloroindol-3-yl]butyric acid (803 mg).

NMR (CDCl₃, δ): 0.88 (12H, d, J=7.5 Hz), 1.70-2.10 (4H, m), 2.32-2.50 (6H, m), 2.65 (2H, t), 5.50 (1H, s), 6.74 (1H, dd, J=2, 8 Hz), 6.83-7.02 (3H, m), 7.06 (4H, d, J=8 Hz), 7.10-7.38 (6H, m), 7.50 (1H d J=2.5 Hz) 8.28 (1H d J=8 Hz).

EXAMPLE 6

The following compounds were obtained according to a similar manner to that of Example 5.

(1) 2-[1-[3-[Bis(4-isobutylphenyl)methylamino]benzoyl]indol-3-yl]acetic acid mp: 90°-92° C.

NMR (CDCl₃, δ): 0.90 (12H, d, J=7Hz), 1.87 (2H, m), 2.47 (4H, d, J=7Hz), 3.70 (4H, s), 5.53 (2H, s), 7.13 (4H, d, J=7.5 Hz), 7.26 (4H, d, J=7.5 Hz), 6.8 (1H, m), 6.9-7.0 (1H, m), 7.0-7.1 (1H, m), 7.2-7.5 (4H, m), 7.6 (1H, m), 8.40 (1H, d, J=8 Hz).

(2) 3-[1-[3-[Bis(4-isobutylphenyl)methylamino]benzoyl]indol-3-yl]propionic acid mp: 73°-76° C.

CDCl₃, δ): 0.88 (12H, d, J=7Hz), 1.83 (2H, m), 2.43 (4H, d, J=7 Hz), 2.69 (2H, t, J=7.5 Hz), 2.97 (2H, t, J=7.5 Hz), 5.50 (1H, s), 6.7-6.8 (1H, m), 6.9-7.0 (2H, m), 7.10 (4H, d, J=8 Hz), 7.25 (4H, d, J=8 Hz), 7.1-7.5 (4H, m), 7.5-7.6 (1H, m), 8.3-8.4 (1H, m).

(3) 5-[1-[3-[Bis(4-isobutylphenyl)methylamino]benzoyl]-indol-3-yl]valeric acid mp: 70°-73° C.

NMR (CDCl₃, δ): 0.89 (12H, d, J=7 Hz), 1.6-1.8 (2H, m), 1.8-2.0 (2H, m), 2.3-2.5 (2H, m), 2.45 (4H, d, J=7 Hz), 2.6-2.7 (2H, m), 5.50 (1H, s), 6.73 (1H, m), 6.93 (1H, m), 6.99 (1H, m), 7.10 (4H, d, J=8 Hz), 7.24 (4H, d, J=8 Hz), 7.0-7.2 (1H, m), 7.2-7.4 (3H, m), 7.52 (1H, m), 8.35 (1H, m).

(4) 6-[1-[3-[Bis(4-isobutylphenyl)methylamino]benzoyl]indol-3-yl]hexanoic acid mp: 65°-70° C.

NMR (CDCl₃, δ): 0.88 (12H, d, J=7 Hz), 1.3-1.5 (2H, m), 1.6-1.8 (4H, m), 1.82 (2H, m), 2.34 (2H, t, J=7

Hz), 2.44 (4H, d, J=7 Hz), 2.63 (2H, t, J=7 Hz), 5.50 (1H, s), 6.73 (1H, d, J=7.5 Hz), 7.08 (4H, d, J=8 Hz), 7.23 (4H, d, J=8 Hz), 6.9-7.4 (6H, m), 7.52 (1H, m), 8.35 (1H, d, J=7.5 Hz).

(5) 4-[1-[3-Bis(4-isobutylphenyl)methylamino]benzyl-]indol-3-yl]butyric acid

NMR (CDCl₃, δ): 0.88 (12H, d, J=7.5 Hz), 1.7-2.0 (2H, m), 1.9-2.2 (2H, m), 2.3-2.5 (2H, t, J=7.5 Hz), 2.43 (4H, d, J=7 Hz), 2.82 (2H, t, J=7.5 Hz), 5.12 (2H, s), 5.35 (1H, s), 7.0-7.3 (5H, m), 6.28 (1H, br s), 6.43 (1H, t, J=8 Hz), 6.86 (1H, s), 7.06 (4H, d, J=8 Hz), 7.19 (4H, d, J=8 Hz), 7.59 (1H, m)

EXAMPLE 7

To a solution of 4-[1-(4-aminobenzoyl)indol-3-yl]-butyric acid (1.5 g) and pyridine (0.91 g) in dichloromethane (15 ml) was added a solution of bis(4-n-propylphenyl)methyl bromide (2.29 g) in dichloromethane (10 ml). The mixture was stirred at room temperature for 1 hour and poured into diluted hydrochloric acid. The separated organic layer was washed with water, dried over magnesium sulfate and evaporated. The residue was purified by chromatography on silica gel (50 g) using chloroform plus 2% methanol as the eluent. Appropriate fractions were combined and evaporated to give 4-[1-[4-bis(4-n-propylphenyl)methylamino]benzoyl]indol-3-yl]butyric acid (1.47 g).

NMR (CDCl₃, δ): 0.96 (6H, t, J=7.5 Hz), 1.5-1.7 (4H, m), 1.9-2.1 (2H, m), 2.42 (2H, t, J=7 Hz), 2.48 (4H, t, J=8 Hz), 2.77 (2H, t, J=7 Hz), 5.56 (1H, s), 6.59 (2H, d, J=9 Hz), 7.1-7.7 (14H, m), 8.28 (1H, dd, J=1, 8.5 Hz).

EXAMPLE 8

The following compound was obtained according to a similar manner to that of Example 7.
4-[1-[4-[Bis(4-isobutylphenyl)methylamino]benzoyl]indol-3-yl]butyric acid NMR (CDCl₃, δ): 0.90 (12H, d, J=7.5 Hz), 1.9-1.7 (2H, m), 2.1-1.9 (2H, m), 2.5-2.4 (2H, m), 2.47 (4H, d, J=7.5 Hz), 2.76 (2H, t, J=7.5 Hz), 5.58 (1H, s), 6.58 (2H, d, J=8 Hz), 7.4-7.0 (10H, m), 7.7-7.5 (4H, m), 8.28 (1H, d, J=8 Hz).

EXAMPLE 9

To a solution of 4-[1-[3-[bis(4-isobutylphenyl)methylamino]benzoyl]indol-3-yl]butyric acid (35.0 g) in isopropyl ether (150 ml) was added 1,4-dioxane solution of 4N hydrogen chloride (15 ml) at 0° C., and the mixture was allowed to stand in a refrigerator overnight. The precipitates were collected by filtration and washed with isopropyl ether to give 4-[1-[3-bis(4-isobutylphenyl)methylamino]benzoyl]indol-3-yl]butyric acid hydrochloride (25.3 g) as pale yellow crystals.

mp: 130° C.

NMR (CDCl₃, δ): 0.80 (12H, d, J=7.5 Hz), 1.75 (2H, m), 2.05 (2H, m), 2.35 (2H, m), 2.35 (4H, d, J=7.5 Hz), 2.70 (2H, t, J=7.5 Hz), 5.55 (1H, s), 6.85 (1H, s), 7.00 (4H, d, J=8 Hz), 7.48 (4H, d, J=8 Hz), 7.4-7.8 (7H, m), 8.42 (1H, dd, J=8, 15 Hz).

We claim:
1. A compound of the formula:

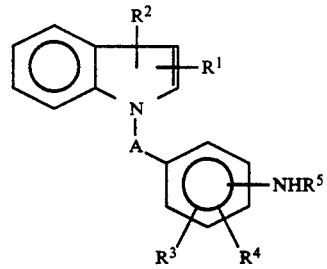

where
R¹ is carboxyl(lower)alkyl or protected carboxy(lower)alkyl,
R² is hydrogen, lower alkyl or halogen,
R³ and R⁴ are each hydrogen or lower alkyl,
R⁵ is ar(lower)alkyl which may have substituent(s) selected from lower alkyl and halogen, and
A is carbonyl, sulfonyl or lower alkylene, wherein lower alkyl and lower alkylene are from 1 to about 6 carbon atoms, or a pharmaceutically acceptable salt thereof.

2. A compound of claim 1, wherein
R⁵ is mono or di or triphenyl(lower)alkyl substituted by a group selected from lower alkyl and halogen.

3. A compound of claim 2, wherein
R⁵ is benzhydryl substituted by a group selected from lower alkyl and halogen.

4. A compound of claim 3, wherein
R¹ is carboxymethyl, carboxyethyl, carboxypropyl, carboxybutyl or carboxypentyl,
R² is hydrogen, methyl or chloro,
R³ and R⁴ are each hydrogen or methyl, and
R⁵ is bis(propylphenyl)methyl, bis(isobutylphenyl)methyl or bis(chlorophenyl)methyl.

5. A compound of claim 4, wherein
R², R³ and R⁴ are each hydrogen, and
A is carbonyl.

6. A compound of claim 5, which is 4-[1-[3-[bis(4-isobutylphenyl)methylamino]benzoyl]indol-3-yl]butyric acid or its hydrochloride.

7. A process for preparing a compound of the formula:

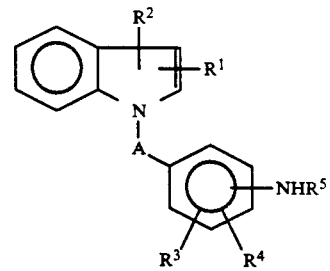

where
R¹ is carboxyl(lower)alkyl or protected carboxy(lower)alkyl,
R² is hydrogen, lower alkyl or halogen,
R³ and R⁴ are each hydrogen or lower alkyl,
R⁵ is ar(lower)alkyl which may have substituent(s) selected from lower alkyl and halogen, and
A is carbonyl, sulfonyl or lower alkylene, wherein lower alkyl and lower alkylene are from 1 to about 6 carbon atoms, or a salt thereof, which comprises reacting in a solvent a compound of the formula:

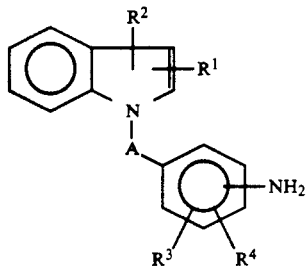

wherein $R^1$, $R^2$, $R^3$, $R^4$ and A are each as defined above, or a salt thereof, with a compound of the formula:

X—$R^5$ wherein $R^5$ is as defined above, and
X is a pharmaceutically acceptable acid residue.

8. A pharmaceutical composition comprising an effective amount of a compound of claim 1 or pharmaceutically acceptable salt thereof in association with a pharmaceutically acceptable substantially non-toxic carrier or excipient.

9. A method for treating or preventing testosteron 5α-reductase mediated diseases, which comprises administering an effective amount of a compound of claim 1 or pharmaceutically acceptable salt thereof to a human being or animal.

* * * * *

UNITED STATES PATENT AND TRADEMARK OFFICE
CERTIFICATE OF CORRECTION

PATENT NO. : 5,283,251
DATED : February 1, 1994
INVENTOR(S) : Satoshi OKADA, et al.

It is certified that error appears in the above-indentified patent and that said Letters Patent is hereby corrected as shown below:

On the title page, Item [21], [22], [86], and [87], the PCT
   information has been omitted, should read as follows:

```
--[21] Appl. No.:         920,384
  [22] PCT Filed:         Feb. 21, 1991
  [86] PCT No.:           PCT/JP91/00218
       § 371 Date:        Oct. 8, 1992
       § 102(e) Date:     Oct. 8, 1992
  [87] PCT Pub. No.:      WO91/13060
       PCT Pub. Date:     Sept. 5, 1991--
```

Signed and Sealed this

Twenty-eighth Day of June, 1994

Attest:

BRUCE LEHMAN

*Attesting Officer*   *Commissioner of Patents and Trademarks*